(12) United States Patent
Cohen

(10) Patent No.: US 8,197,433 B2
(45) Date of Patent: Jun. 12, 2012

(54) EAR TUBES

(75) Inventor: David Cohen, Jerusalem (IL)

(73) Assignee: Otomedics Advanced Technologies, Ltd., Jerusalem (IL)

( * ) Notice: Subject to any disclaimer, the term of this patent is extended or adjusted under 35 U.S.C. 154(b) by 708 days.

(21) Appl. No.: 11/917,751

(22) PCT Filed: Jun. 15, 2006

(86) PCT No.: PCT/IL2006/000689
§ 371 (c)(1),
(2), (4) Date: Aug. 13, 2008

(87) PCT Pub. No.: WO2006/137054
PCT Pub. Date: Dec. 28, 2006

(65) Prior Publication Data
US 2009/0088677 A1   Apr. 2, 2009

(30) Foreign Application Priority Data

Jun. 20, 2005 (IL) .......................................... 169297
Jun. 12, 2006 (IL) .......................................... 176251

(51) Int. Cl.
*A61M 5/00* (2006.01)
(52) U.S. Cl. ........................................... 604/8; 606/109
(58) Field of Classification Search ........... 604/8, 96.01, 604/509, 510; 606/2, 162; 128/207.18
See application file for complete search history.

(56) References Cited

U.S. PATENT DOCUMENTS

| | | |
|---|---|---|
| 4,695,275 A | 9/1987 | Bruce et al. |
| 5,246,455 A | 9/1993 | Shikani |
| 5,645,584 A | 7/1997 | Suyama |
| 5,775,336 A | 7/1998 | Morris |
| 6,042,574 A | 3/2000 | O'Halloran |
| 6,638,233 B2 * | 10/2003 | Corvi et al. .................... 600/564 |
| 7,704,259 B2 | 4/2010 | Kaplan et al. |
| 7,727,186 B2 * | 6/2010 | Makower et al. .......... 604/96.01 |
| 2002/0058898 A1 | 5/2002 | Goode et al. |
| 2002/0147441 A1 | 10/2002 | Reisdorf et al. |
| 2003/0018291 A1 * | 1/2003 | Hill et al. ......................... 604/8 |

OTHER PUBLICATIONS

Schweinfurth et al, "Middle Ear, Tympanic Membrane, Infections", Copyright 1994-2011, http://emedicine.medscape.com/article/858558-overview.*

"Triune Tube". Product pamphlet for tympanoplasty tube manufactured by Grace Medical. Downloaded from http://gracemedical.com/wp-content/uploads/2011/04/LIT0056-CID2892-Triune-Salesheet.pdf on Nov. 7, 2011. According to a company spokesman, the product has been sold since about 2002.

* cited by examiner

*Primary Examiner* — Melanie Hand
(74) *Attorney, Agent, or Firm* — Kilpatrick Townsend & Stockton LLP

(57) ABSTRACT

The invention provides a flexible ear tube (10) for draining and ventilating the middle ear, the tube (10) having a flexible substantially tubular stem (12) with a lumen (14), the stem (12) being sized to be inserted through an incision in the eardrum (16) and the tube having at least two separate flexible contact surfaces (18) extending from the stem (12) and adapted to engage different spaced-apart inner surfaces of the eardrum 16, each of the contact surfaces (18) having a first axis XX extending substantially perpendicularly to the central axis of the stem and a second axis YY extending substantially perpendicularly to the first axis wherein one of the axes is between 0.6 and 3 mm and the second of the axes is between 1 and 7 mm in length.

29 Claims, 7 Drawing Sheets

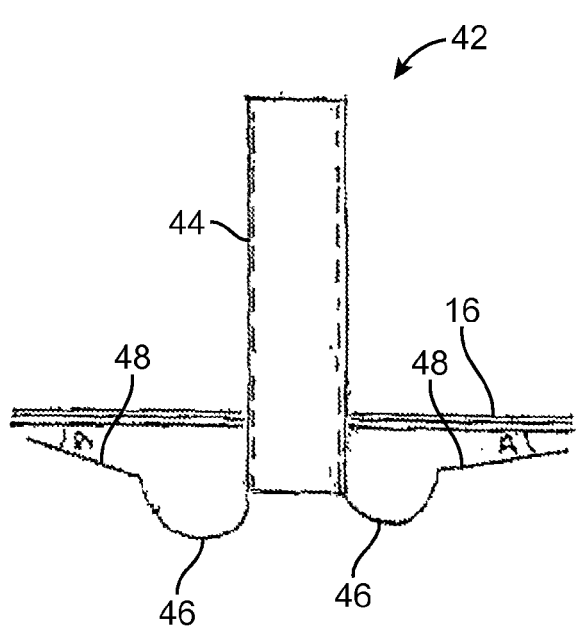
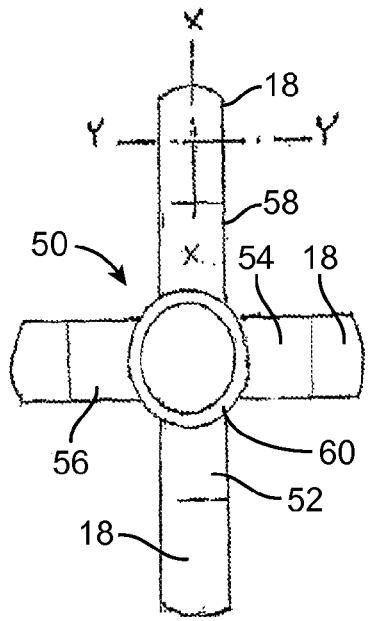
FIG. 5　　　　　FIG. 6
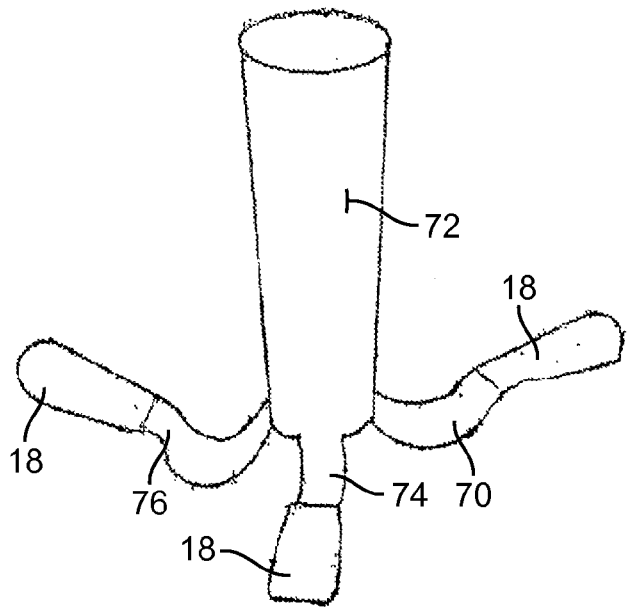
FIG. 7

EAR TUBES

The present invention relates to ear tubes. In particular, the present invention relates to tubes for draining fluid through the eardrum or ventilating the middle ear cavity, and device and method of inserting the tube into an ear. In particular, the invention relates to an easily inserted and removed tube, with long durability and minimal damage to the eardrum. A one-step introducer makes the insertion feasible as an outpatient procedure suitable for the treatment of all kinds of middle ear ventilation and drainage problems.

BACKGROUND OF THE INVENTION

Typically, pressure and drainage of fluids within the middle ear are influenced by the Eustachian tube and gas regulation in the middle ear cavity. When this regulation is not functioning properly, the pressure within the middle ear tends to drop, interfering with the drainage of the fluid by the Eustachian tube. The results of this pathology are accumulation of fluid, middle ear infections (mainly in infants), and sometimes retraction of the eardrum. All these conditions cause loss of hearing, infections endangering the ear, severe pain mostly in infants, destruction of major structures of the middle ear and other complications.

In order to ventilate the middle ear and enable drainage, ear tubes were found to be the best efficient solution, and are advantageous compared to other medical methods. However, their insertion needs minor surgical procedure, frequently under general anesthesia (mainly in children). Other disadvantages of tubes are damage to the eardrum and lack of control of the stay of the rigid type of tubes.

The tube provides gas supply to the middle ear and drains pus when present. Preventing the accumulation of fluid reduces the risk for infection.

Tubes with small internal diameter (I. D.) of less than 1.0 mm tend to clog with secretions. The long narrow shaft of the long standing T-tubes is unsuitable for draining pus. The wider I. D. (>1.2 mm) of the rigid tubes is better, but these kinds of tubes have other disadvantages, such as short-term longevity and difficult extrusion.

To install a tube, a small incision is made in the eardrum and the tube is inserted therethrough.

There are various types of ear tubes. They can be divided into two major groups: rigid (or semi-rigid) and flexible.

The rigid types basically with the form of a bobbin, first designed by Armstrong (1954), are available in many varieties. They are made of polyethylene, silicone, metals and other inert materials and produced by many manufacturers. They are formed as a shank with a trailing flange. Retention of this kind of tube is unpredictable. It tends to fall out of the ear after about a year, and there is no way to ensure its retention. It may fall out within days or last for years.

The flexible type of ear tubes, commonly called a T-tube on account of its shape (first designed by Goode), stays longer and is easy to remove, but needs repeated cleanings by a physician and has up to a 20% rate of causing permanent perforation in the eardrum. The flange of the T-tube unfolds at an angle of 90° to its axis. The flange creates pressure on the eardrum in the area close to its insert and erodes it, causing perforation, frequently permanent.

Sometimes T-tubes tend to shift and align themselves across the ear canal or block the tube, thereby making the checking thereof or the access to its lumen difficult.

Another disadvantage of the T-tubes is the difficulty of insertion. This procedure takes longer and is more painful, and needs general anesthesia in children and even in some of adult patients.

Both the rigid and the T-type tubes cause thinning of the eardrum at the site of the insertion in more than 20% of the cases in addition to the tendency to perforate the eardrum. This is also a result of the interaction between the edges of the tube and the rim of the eardrum-perforation in which it sits.

In thin eardrums neither tube is retained, and falls out shortly after insertion. In this condition there is a high probability for the occurrence of a permanent perforation. The T-tube does provide some support, though only for a limited thinned area.

In cases where the eardrum is very thin and retracted on the medial wall of the middle ear cavity, adhesion between the eardrum and the medial wall occurs, causing loss of hearing and destruction of principal structures of the middle ear. This may lead to a destructive process inside the middle ear called cholesteatoma.

All the tubes have their contact with the eardrum at the rim of the perforation. For example, the 'bobbin' type is described e.g. in U.S. Pat. No. 4,174,716, and U.S. Pat. No. 4,468,218, the 'T' type is described in U.S. Pat. No. 4,695,275 and US2004/0077989, and a V-shaped type is described in U.S. Pat. No. 4,808,171. None of said patents or applications, however, teach or suggest a contact area which is distant from the rim of the perforation. Since the tube is slowly pulled away from the eardrum by the external layer of the epithelium advancing over its surface, the point of maximal pressure on the eardrum is at the anchoring collar of the tube, at the rim of the perforation. At this point exists the highest pressure on the tissue. This problem is found in all the tubes and is the cause for perforations and granulation tissue.

There is a need for an improved ear tube that can be easily inserted, easily removed according to the physician decision, suitable for draining pus from infected middle ear (acute otitis media) or ventilating poorly ventilated ears (otitis media with effusion), quickly and easily inserted (preferably as an outpatient procedure), stays in place as long as required, does not tend to cause permanent perforations in the eardrum, stays perpendicular to the ear drum and can readily been cleared if it becomes obstructed, supports thin parts of the eardrum (preventing adhesions), can be anchored even in a thin eardrum, and provides for good visibility during the insertion procedure for a better and more accurate placing.

OBJECTS OF THE INVENTION

The object of the invention is to create an easy to insert, easy to remove, suitable for outpatient procedure, long standing, well ventilating and draining, easy to clean ventilating tube, well tolerated by the eardrum and with ability to support retracted thin eardrum.

SUMMARY OF THE INVENTION

Structure

Thus according to the present invention there is now provided a flexible ear tube for draining and ventilating the middle ear, said tube having a flexible substantially tubular stem with a lumen, said stem being sized to be inserted through an incision in the eardrum and said tube having at least two separate flexible contact surfaces extending from said stem and adapted to engage different spaced-apart inner surfaces of said eardrum, each of said contact surfaces having a first axis extending substantially perpendicularly to the central axis of said stem and a second axis extending substantially perpendicularly to said first axis wherein one of said axes is between 0.6 and 3 mm and the second of said axes is between 1 and 7 mm, preferably between 1 and 6 mm and most preferred between 1 and 4 in length.

In preferred embodiments of the present invention the ratio of the lengths of said axes is between 1:6 and 1:1.

In especially preferred embodiments of the present invention each of said separate flexible contact surfaces has a substantially flat contact surface area of at least 1 mm$^2$.

In more preferred embodiments of the present invention each of said separate flexible contact surfaces has a substantially flat contact area of at least 1.5 mm$^2$.

In the most preferred embodiments of the present invention each of said separate flexible contact surfaces has a substantially flat contact surface area of at least 2 mm$^2$.

In other preferred embodiments of the present invention, there is provided a flexible ear tube for draining and ventilating the middle ear, said tube having a flexible, substantially tubular stem with a lumen, said stem being sized to be inserted through an incision in the eardrum and said tube having at least two flexible anchoring means attached to the outer periphery of said stem, each of said anchoring means being provided with contact surfaces adapted to engage an inner surface of the perforated eardrum, said contact surfaces being spatially removed and spaced apart from the outer perimeter of said stem.

Obviously said tubular stem can have a circular or rectangular cross section and can be cylindrical or conical in configuration.

In preferred embodiments of the present invention said anchoring means comprise at least two spaced-apart non-linear arms extending from said stem.

In said preferred embodiments of the present invention each of said arms ascribes a substantially concave, sometimes twisted arch between its point of contact with said stem and the contact surface provided at the distal end thereof relative to the inner surface of the perforated eardrum upon insertion of the flexible ear tube.

In other preferred embodiments of the present invention each of said arms ascribes an angle between its point of contact with said stem and the contact surface provided at the distal end thereof, said angle facing towards the inner surface of the perforated eardrum upon insertion of the flexible ear tube and the apex of said angle being spatially removed from said eardrum.

In some of the preferred embodiments of the present invention said ear tube is provided with a pair or more of opposed arched arms, symmetric or asymmetric, extending from one end of the stem.

In other preferred embodiments of the present invention said flexible ear tube comprises more than two asymmetric arms extending from said stem, said arms including a first longer arm adapted upon insertion to be directed towards the anterior part of the tympanic cavity, and other arms of variable length to be directed towards the posterior part of the tympanic cavity as well as being directed towards other directions within said cavity.

In an especially preferred embodiment of the present invention there is provided a flexible ear tube comprising four asymmetric arms extending from said stem, said arms including a first longer arm adapted upon insertion to be directed towards the anterior part of the tympanic cavity, a pair of relatively shorter arms adapted upon insertion to be directed superiorly within the tympanic cavity and a fourth medium size arm adapted upon insertion to be directed towards the posterior part of the tympanic cavity.

Thus the arms are arched, spiral or angled and project laterally from the end of the said stem that is inserted within the ear, when open. Each arm is bent in the part close to the stem, and carries a flattened facet at its end. The facet can be attached directly to the stem, having the same said variety of shapes but without an arm. The flattened facet is bent to form a 90° angle or less from the stem so that the surface touching the inner aspect of the eardrum is the said flat facet. This flat facet is either of the same width or wider than the bent part of the arm, and has round, oval or other shapes. The bent part of the arm adjacent to the stem and to the rim of the perforation is not in contact with the eardrum. This rim of perforation is left free of any contact. The apex of concavity of the bent arms may touch the medial wall of the middle ear and be supported by it. The general design of the arm provides maximal flexibility independently for each arm, thus preventing any excessive pressure on the contact surface of the eardrum. This construction resembles suspensions of a car wheels. The design distributes the pressure on the contact area of the inner surface of the eardrum to a much larger area and diminishes the forces acting on the tissue and the blood supply of the eardrum. By this means atrophy of eardrum tissue is prevented.

When multiple (four) arms are used they can be asymmetric. They can be designed so that the long arm is directed towards the anterior part or any desired direction of the tympanic cavity (the middle ear space), other arms are directed superiorly, inferiorly or posterior. This positioning assists in locating the tube in the posterior part of the eardrum where the regeneration ability is better, and avoiding insertion in the anterior part of the eardrum where the regeneration ability and the spontaneous closure of perforations are less favorable. By this it reduces the possibility for a permanent perforation of the eardrum. Yet it assists in holding the tube in place using that anterior area for further support, without creating any pressure on it.

When a pair of arms is used, they are directed symmetrically to the two sides of the said shaft end, having the same said arched structure but may differ in length.

The stem of the tube is of cylindrical, rectangular or conical shape. When conical or rectangular the wider end (base of cone) is adjacent to the free end thereof, thus making the cleaning of its lumen easier. When rectangular, the walls of the longitudinal stem can also be parallel.

The stem is made with a wide or a narrow internal diameter. The tube with the wide diameter is for good drainage of pus in infected conditions, while the narrow one is for ventilation only.

In preferred embodiments of the present invention, said anchoring means are respectively attached to said stem by non-linear arms and each of said arms is provided with a configuration selected from the group consisting of arched, sometimes twisted arms and angled arms to assure that the respective segments of the respective arms that extend from the stem to the anchoring means is not in contact with the eardrum upon insertion of the ear tube according to the present invention.

Another feature of the present invention is the use of at least two flattened facets with or without bent arms, anchoring the tube within the eardrum together with significant reduction of the pressure created on the inner surface of the eardrum. As a result, the incidence of perforations in the eardrum or thinning of it is greatly reduced.

The number of arms contributes to the stability of the ear tube within the eardrum and gives a good support to thin areas thereof. The physician can choose the desired kind of tube (size and number of arms) according to the ear's condition. The physician can also trim part of the facets, arms or shaft according to requirements, thereby improving the match between the tube and the eardrum.

The good support of thinned areas of the eardrum also helps in separating or preventing potential adhesions between the eardrum and the medial wall of the middle ear. The outer aspect of the arch rests on the medial wall of the middle ear, elevating the said facet (and the eardrum together with it) to a better position, with a gap from the medial wall of the middle ear. This quality is very important in thinned eardrums that otherwise may need surgical correction of the eardrum. Providing support to thin eardrum is a unique quality of the tube according to the present invention.

The configuration that enables the tube to remain vertical to the eardrum and consequently is not blocked by the external ear canal wall is another important feature of the present invention. The physician can look down the lumen of the tube to detect and clean any obstructions, as well as to look inside the middle ear cavity.

Another quality of the tube is the conical shape of the stem. This shape eases the cleaning thereof.

The tube is made of a colored or translucent soft flexible material, preferably silicone.

Insertion:

In preferred embodiments of the present invention there is provided a flexible ear tube as hereinbefore defined in combination with a flexible sleeve having a lumen sized to receive said tube comprising said stem and said anchoring means, said sleeve being provided with an open end through which said tube is inserted into a perforated eardrum.

In especially preferred embodiments of the present invention there is provided a combination of said flexible ear tube in combination with said flexible sleeve further comprising an introducer means wherein said sleeve and said introducer means are provided with interlocking means and said introducer means includes an element sized to be inserted within the lumen of said sleeve and to exert an axial displacement force against said tube to expel the same from the sleeve and into a perforated eardrum.

In another preferred embodiment of the present invention the tube is wrapped in a way that the arms are compressed in a spiral-like form to enable resilient opening of the arms at the very beginning of the introduction. Such a spiral method of packing is preferably used inside the sleeve.

In another preferred embodiment of the present invention the tube is mounted on the end of a plastic introducer equipped with a tiny strip (band) of plastic or metal that holds the tube with its arms closed together. When the tube is pushed inside the perforation in the eardrum it comes out of said strip and implanted in the eardrum.

In preferred embodiments of the present invention said tubular stem is provided with a thin triangular or rectangular side element attached to the outer portion of said stem.

In especially preferred embodiments of the present invention a first support arm of one of said flexible contact faces is of a larger diameter and is stiffer than a second opposite support arm of a second flexible contact face.

Preferably said flexible ear tube is further provided with a bridge member attached to two support arms and an extended tension member firmly attached to said bridge member and extending outwards therefrom.

In especially preferred embodiments of the present invention there is provided a combination of said flexible ear tube with a guide that helps in directing the tube into the hole created in the eardrum. Said guide has an elongated 'tail' held by the surgeon and a curved holder that holds the tube and eases its insertion.

The tube is inserted inside a semi lunar shaped end of a plastic or a steel wire guide so that the end with the arms points towards the end of the guide, slightly protruding from it. Insertion is done by grasping the tube together with the guide with an ear forceps, the arms of the tube pointing towards the perforation created in the eardrum. By pushing the tube towards the promontory while holding the guide's tail the tube is inserted into the perforation, and the empty guide is removed.

The guide is made of a plastic or other semi-rigid or rigid material, such as stainless steel wire.

Thus, as will be realized according to its major aspects and broadly stated, the present invention is a flexible ear tube for draining and ventilating the middle ear and a device and a method of insertion. The ear tube includes a cylindrical, rectangular or conical stem having a lumen longitudinally formed therein and a port extending through the surface of the stem for providing access to the lumen. Two or more asymmetric or symmetric bent arms extend from one end of the stem. A flexible translucent sleeve covers the tube for easier insertion. An introducer makes the insertion of the tube an accurate and quick procedure.

The tube is wrapped with its arms within a translucent flexible sleeve (envelope) defined by the outer dimensions of the stem. The sleeve is longer than the tube. The tube is inserted (or packed) inside it so that the shaft is in the middle of the sleeve: the arms are at one end, while the other end of the sleeve is empty. This empty end is mounted over the lip of the introducer, covering its free end. When the tube is inserted into the ear, the arms resiliently spring open through the eardrum to anchor the tube.

When inserted into the sleeve and when the sleeve is mounted on the tip of the introducer, the tube is located in a way that the long arm will be directed towards the desired direction (usually anteriorly).

The invention includes an introducer that may be used in some of the embodiments, in addition to said sleeve and said guide. The introducer comprises a rigid tube bent about 30° to enable visibility of its end when inserted into the ear. The introducer handle has a flat surface and contains a knob attached to the end of a flexible mandrel that passes through the whole length of the shaft. When the knob is pushed forwards the flexible mandrel pushes the tube out of the sleeve to be inserted into its place inside the perforation cut in the eardrum.

Near the tip of the introducer a short projection protrudes from the ventral side of the introducer's shaft. In the sleeve a small hole is created near its empty end so that it fits with the said projection when mounted on the introducer's tip. This projection prevents the sleeve from sliding from the introducer while inserting the tube. The hole in the sleeve is located so that the arms of the tube are arranged in the desired directions to spread out into the ear in the proper position.

The sleeve is generally cylindrical. It may however have a diameter, which is larger in proximity to the handle and smaller towards the operating end.

A major feature of the present invention is the use of a sleeve and an introducer that holds the arms of the ear tube in alignment during the insertion through the eardrum and making the insertion accurate and easy to carry out. Typically, special instruments must be employed to insert other ear tubes having flanges that resiliently spring open. The ear tube sleeve of the present invention provides a simple and effective alternative of keeping the arms of these ear tubes in alignment during their insertion within the eardrum.

Another feature of the present invention is the transparent characteristics of the sleeve, which is made from a thin translucent material. As a result of this feature, the physician can monitor the advance of the tube during its insertion. This helps in the proper positioning of the tube.

A preferred form of an introducer is a stiff plastic rod bent in an angle of more than 90°, with a widened grip on one end to be used as a handle, and a thin transparent plastic sleeve on the other. Said sleeve is of a triangular shape with the base pointing to its outer end, and the margins stacked together to leave a tubular lumen. In said lumen the tube is inserted with its arms slightly protruding and ready to be inserted. To insert the tube the end with the sleeve is applied into the incision and pushed into it. During the insertion said sleeve is soft enough to let the tube pushed out of it into the middle ear cavity. The inserter is then removed and the tube is properly placed using a slender ear forceps.

The Method of Introducing the Tube:

The method of introducing the tube includes the following steps:
1. Cutting a small incision in the desired place in the eardrum;
2. Providing the tube with a sleeve. The tube inside its sleeve is mounted on the tip of the introducer, the arms of the tube are at the other end of the sleeve, in a way that the long arm is directed anteriorly;
3. Placing the end of the introducer with the ear tube thereon within the ear, so that the end of the sleeve is slightly inserted into the eardrum through the perforation; tube and guide are grasped with an ear forceps and the tip of the tube is inserted into the perforation.
4. Pushing the ear tube through the eardrum by sliding the knob of the introducer found at the handle, and
5. Removing the introducer from the ear. Since the sleeve is attached to the tip of the introducer, it is removed together with it from the ear.

When the rod inserter is used the steps are:
  Cutting a small incision in the desired place in the eardrum, to provide an easy insertion;
  Inserting the rod with the tube inside the lumen of the sleeve and pushing it into the middle ear cavity;
  The rod is then removed leaving the tube inside the incision;
  The tube is adjusted in a proper position using a slender ear forceps.

When a guide is used the steps are:
1. Cutting a small incision in the desired place in the eardrum, to provide an easy insertion;
2. The guide with the tube on top inside the semi lunar end is held from its tail with the surgeon's hand. The other end carrying the tube is put near the perforation;
3. The tail of the guide is held fixed to the ear speculum to prevent any further advancement of it;
4. The tube only is pushed with a slender ear forceps and inserted into the said perforation, till the arms resiliently spread to their right position;
5. Holding the tube in place the guide is then removed from the ear;
6. The tube is then properly set in its place.

When the tube is inserted, in cases such as when the patient has a thin eardrum, without the use of the introducer, a sleeve or a guide, the arms are held together with a slender ear forceps, or inserted inside the tip of a suitable different kind of introducer, and pushed inside the perforation created in the eardrum.

Another way of inserting the tube is by holding the free end thereof with a slender forceps and inserting one arm through the perforation, then pushing the whole tube inside the middle ear cavity through the middle this perforation while grasping the free end securely with the forceps. Thereby all the arms will be pushed inside the middle ear cavity. The tube free end is then pulled retrograde to the right position. The arms then spread out and the insertion is then completed. This technique is not recommended for a thin eardrum or should be done gently.

While a double-arm tube can easily be inserted without an introducer using ear forceps, a multiple-arm tube needs the guide or the introducer for its insertion and may need a special spiral way of packing.

An additional practical feature is its easy insertion when the introducer is used. This feature makes the insertion without general anesthesia feasible in cooperative patients of all age groups and makes it useful as an outpatient procedure.

Anesthesia:

The use of inserter, a guide or a sleeve makes the insertion accurate and short. Topical anesthesia may suffice in cooperative patients and enables outpatient conditions.

Removal:

The flexibility of the material enables easy removal.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

In the drawings:

FIG. 5 is an elevational view of an embodiment having arched arms;

FIG. 6 is a plan view of an embodiment provided with arms of different length;

FIG. 7 is a perspective view of a four-arm embodiment;

DETAILED DESCRIPTION OF PREFERRED
EXEMPLARY EMBODIMENTS

Figure 1:
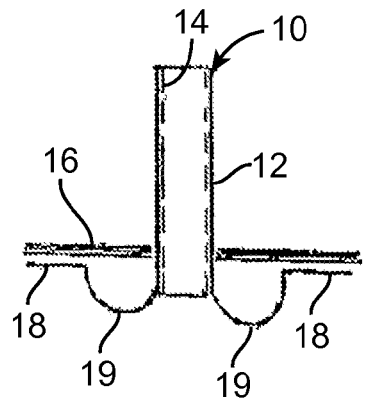
FIG. 1 is an elevational view of a preferred embodiment of the tube according to the invention.

There is seen in FIG. 1 a flexible ear tube 10 for draining and ventilating the middle ear. The tube 10 has a flexible substantially tubular stem 12 with a lumen 14, the stem 12 being sized to be inserted through an incision in the eardrum 16. The tube seen in the figure has two separate flexible contact surfaces 18, extending from the stem 12 by means of anchoring arms, each comprising a contact surface 18 spaced apart from the stem by way of a flexible member 19.

Preferably each of the separate flexible contact surfaces 18 has a substantially flat contact surface area of at least 1 mm$^2$. Advantageously this area is 1.5 mm$^2$, and can even be 2 mm$^2$ or more.

The tube is made of flexible material, for example of silicone rubber or of soft plastic, for example a suitable grade of urethane.

The contact surfaces 18 are adapted to engage different spaced-apart inner surface of the eardrum 16. Each of the contact surfaces 18, as will be seen in FIG. 8, has a first axis XX extending substantially perpendicularly to the central axis of the stem and a second axis YY extending substantially perpendicularly to the first axis. As seen in FIG. 6, the ratio between the axes is between about 1:8 and 1:1. The following are dimensions of the legs that have been used for building prototypes:

|  | Total leg length | Leg width | Platform length |
| --- | --- | --- | --- |
| Minimum (mm) | 2 | 0.6 | 0.5 |
| Maximum (mm) | 7 | 3 | 7 |

With regard to the rest of the figures, similar reference numerals have been used to identify similar parts.

Figure 2:
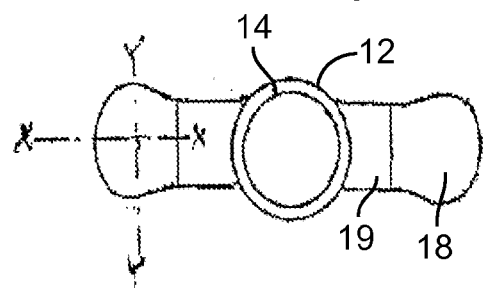
FIG. 2 is a plan view of a two-arm embodiment.

Referring now to FIG. 2 there is seen a further embodiment of a flexible ear tube 20 wherein the ratio of the lengths of the axes XX to YY is between 1:4 and 1:1.

Figure 3:
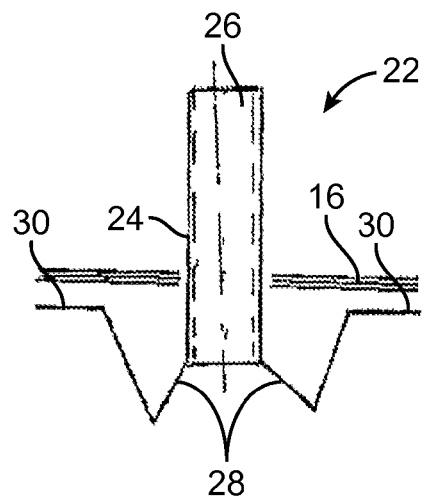
FIG. 3 is an elevational view of an embodiment wherein the arms are sharply bent.

FIG. 3 illustrates a further flexible ear tube 22. The tube has a flexible, substantially tubular stem 24 with a lumen 26, the stem 24 being sized to be inserted through an incision in the eardrum 16. The tube 22 has two flexible anchoring strips or arms attached to the outer periphery of the stem 24, each of the anchoring strips being provided with a flexible member 28 and a contact surface 30.

The contact surfaces 30 are spatially removed and spaced apart from the outer perimeter of the stem 24 by way of the flexible member 28, and are adapted to engage an inner surface of the perforated eardrum 16.

Figure 4:
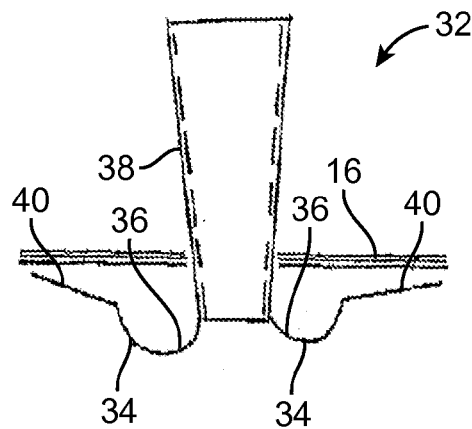
FIG. 4 is an elevational view of an embodiment having a tapered tube.

Seen in FIG. 4 is an embodiment of the flexible ear tube 32 wherein each of the arms 34 ascribes a substantially concave arch 36 between its line of contact with the stem 38. The contact surface 40 is provided at the distal end of the arm 34 relative to the inner surface of the perforated eardrum 16 upon insertion of the flexible ear tube 32. It will be noticed that in the present embodiment the stem 38 has the form of an inverted truncated cone.

Turning now to FIG. 5 (seen also in FIG. 1), there is depicted a further embodiment of a flexible ear tube 42 for draining and ventilating the middle ear. The tube has a flexible, tapered stem 44 with a lumen 45, and the stem 44 is sized to be inserted through an incision in the eardrum 16.

The stem 44 has two flexible anchoring arms 46 attached to its outer periphery. Each of the anchoring arms 46 is provided with contact surfaces 48 adapted to engage an inner surface of the perforated eardrum 16. The contact surfaces 48 are spatially removed and spaced apart from the outer perimeter of the stem 44.

In the present embodiment each arm 46 ascribes an angle between its line of contact with the stem 44. The contact surface 48 is provided at the distal end of the arm 46.

Due to flexibility the whole surface 48 comes in contact with the eardrum 16. In the shown embodiment the two arms 46 are symmetrically disposed.

FIG. 6 shows a further flexible ear tube 50 comprising four asymmetric arms 52, 54, 56, 58, extending from the stem 60. The arms include a first longer arm 52 adapted upon insertion to be directed towards the anterior part of the tympanic cavity. A pair of shorter arms 54, 56 are adapted upon insertion to be directed superiorly and inferiorly within the tympanic cavity. A fourth medium size arm 58 is adapted upon insertion to be directed towards the posterior part of the tympanic cavity.

FIG. 7 illustrates a flexible ear tube 68 comprising four asymmetric arms 70,74,76 extending from the stem 72. The arms include a first longer arm 70 adapted upon insertion to be directed towards the anterior part of the tympanic cavity. The two remaining arms 74, 76 are of variable length and are adaptable to be directed towards the posterior part of the tympanic cavity. The arms 70, 74, 76 are sufficiently flexible to allow the physician to adapt said arms to suit the shape of the tympanic cavity as required (this is true for FIG. 5 as well).

Figure 8:
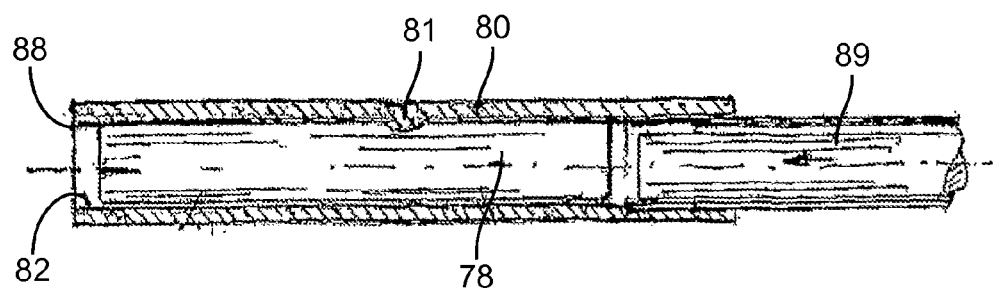
FIG. 8 is a cross-sectional view of a tube useful for inserting the tube into the ear.

Turning now to FIG. 8, there is depicted a flexible ear tube 78 in combination with a flexible sleeve 80 having a lumen 82 sized to receive the tube 78 and 86. The sleeve 80 is provided with an open end 88 through which the tube 78 is insertable into a perforated eardrum.

In the shown preferred embodiment the sleeve 80 is of the same length, shorter or longer than the tube 78. A detent 81 temporarily retains the tube 78. The tube 78 can however be pushed out of the sleeve 80 by use of the pushrod 89. The extra length of the sleeve is for the tip of the introducer.

Figure 9:
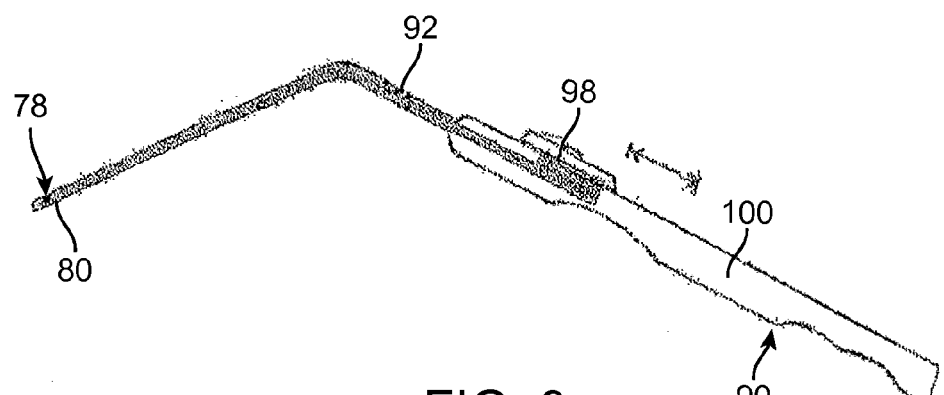
FIG. 9 is an elevational view of an instrument for easing the task of ear insertion.

FIG. 9 shows the flexible ear tube 78, seen to better effect in FIG. 8, in combination with a flexible sleeve 80 and further comprising an introducer 90. The sleeve 80 and the introducer 90 are provided with interlocking means (not seen). The introducer 90 includes a flexible mandrel element 92 sized to enter the lumen 82, seen in FIG. 8, of the sleeve 80 and to exert a displacement force against the tube 78 to expel the same from the sleeve 80 and into a perforated eardrum. The mandrel 92 is advanced by means of a slider button 98, supported on handle 100.

Figures 10, 11, 12:
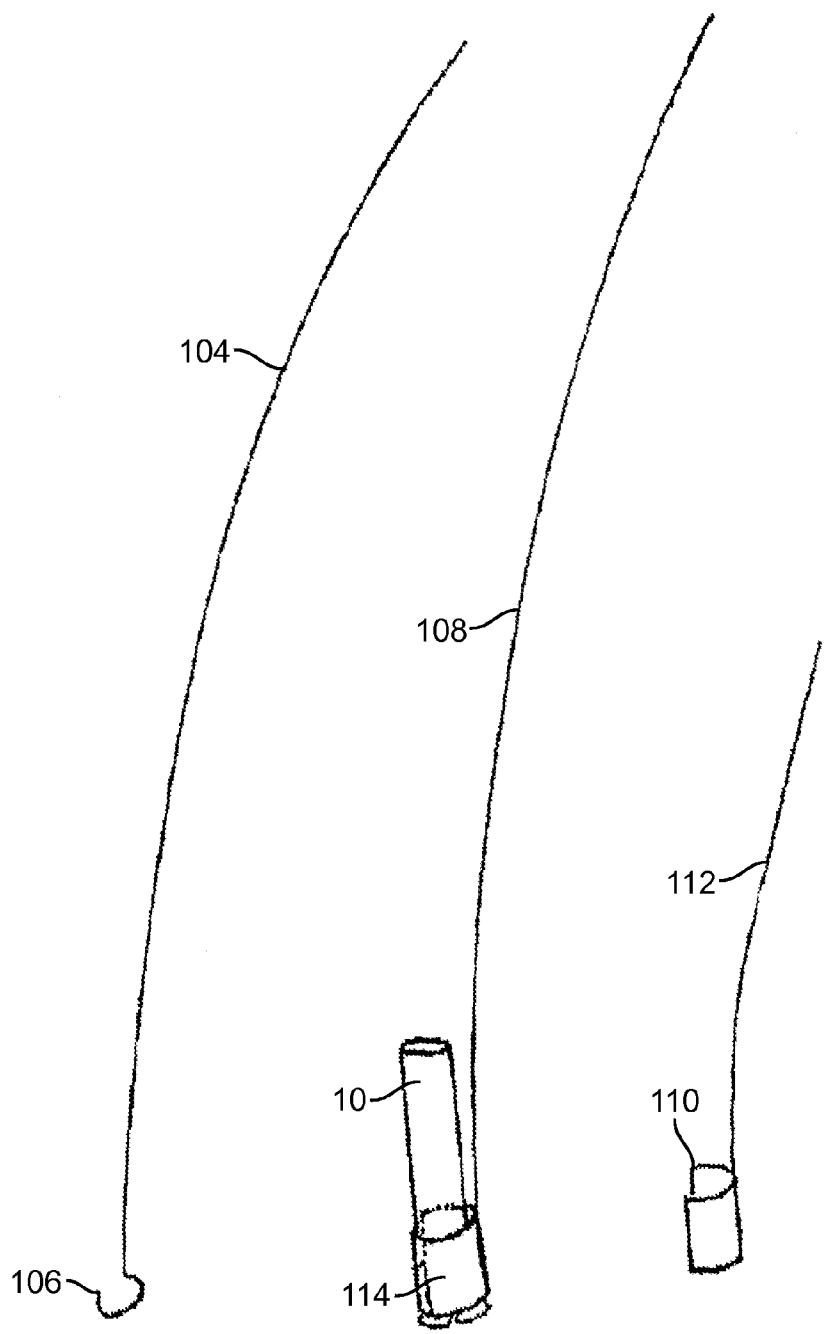
FIGS. 10, 11, and 12 are perspective views of wires arranged to manipulate the ear tube during insertion.

FIG. 10 shows a manipulation wire 104 extending at least 3 cm outside the ear (not shown) of a patient. The wire can be removably attached to a flexible ear tube, and has a Looped form 106 at one extremity.

In FIG. 11 a manipulation plastic guide having a cylindrical grip at one end. The flexible ear tube 10 is slidably disposed inside the guide tube 106, the guide tube being withdrawn by means of the guide 108 attached thereto. The open guide tube 110 is useful for gripping flexible ear tubes 10, seen in FIG. 1. The open guide tube 110 is useful where there are variations in the outer diameter of the flexible ear tube to be handled.

FIGS. 11 and 12 are the same device. The device is made of plastic material with flattened grip at the end.

Figures 13A, 13B:
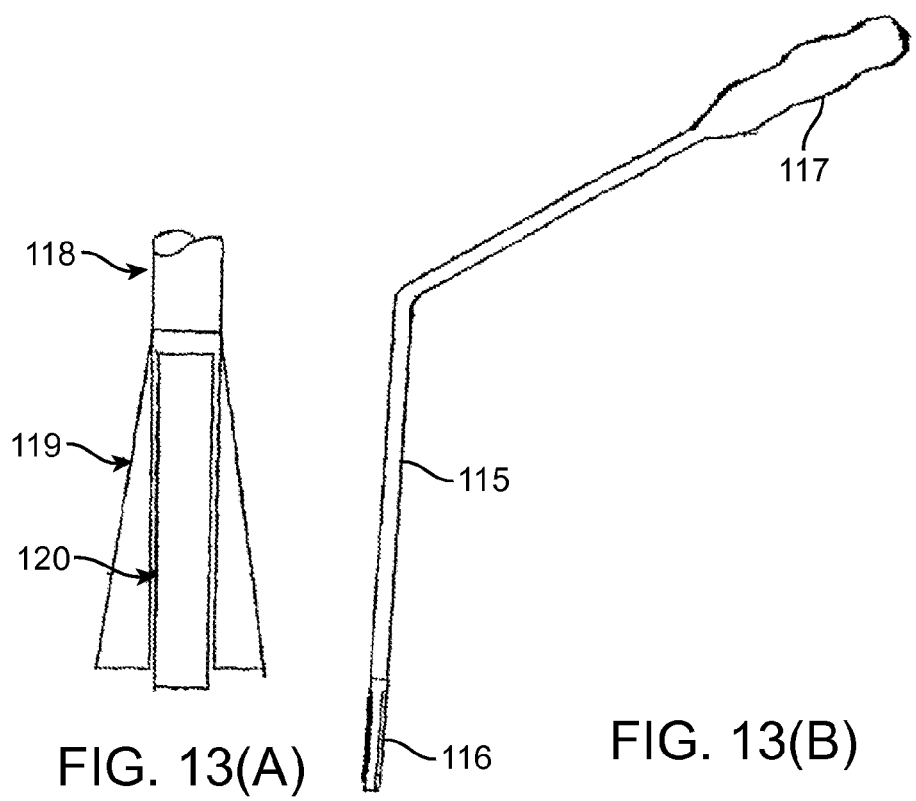
FIGS. 13(A) and 13(B) are elevational views of an instrument for easing the task of ear insertion having a sleeve at its tip.

In FIGS. 13(A) and 13(B), a rod inserter 115 with a handle 117 and with a plastic thin sleeve (front and side views—116 and 119) is seen. The sleeve is attached to the end of the rod 118. The tube 120 is inserted inside the sleeve's lumen. The sides of the sleeve 116 and 119 are glued to each other to form a plain sheet.

Figure 14:
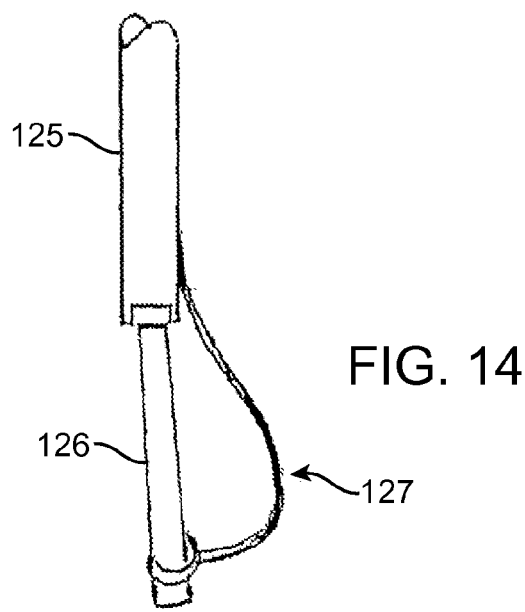
FIG. 14 is an elevational view of the tip of a rod provided with a strip to hold the tube's arms close together to ease the insertion.

In FIG. 14 another kind of introducer with a tiny plastic band 127 at the distal end of it 125, holding the tube 126, is seen—ready for insertion. The distal end 125 of the tube 126 slightly projects from the end of the introducer.

Figure 15:
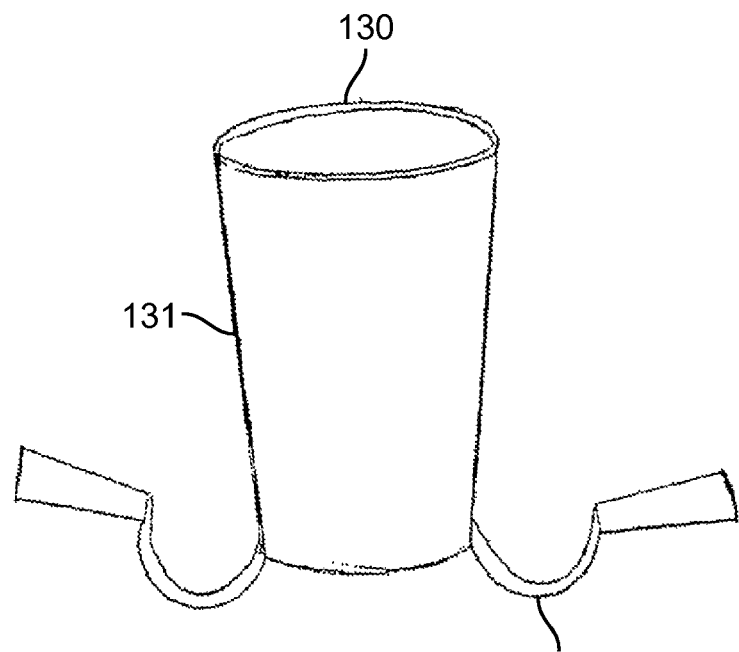
FIG. 15 is an elevational view of a double arm tube.

FIG. 15 shows a 3-dimensional view of a bipedicle tube. The inner diameter of the stem is wide at its free end 130 making a tapering shaft 131, as noted in the drawing, or can be narrower (between 1.3 mm at the free end and 1.0 mm at the other end, near the arms 132).

Figure 16:
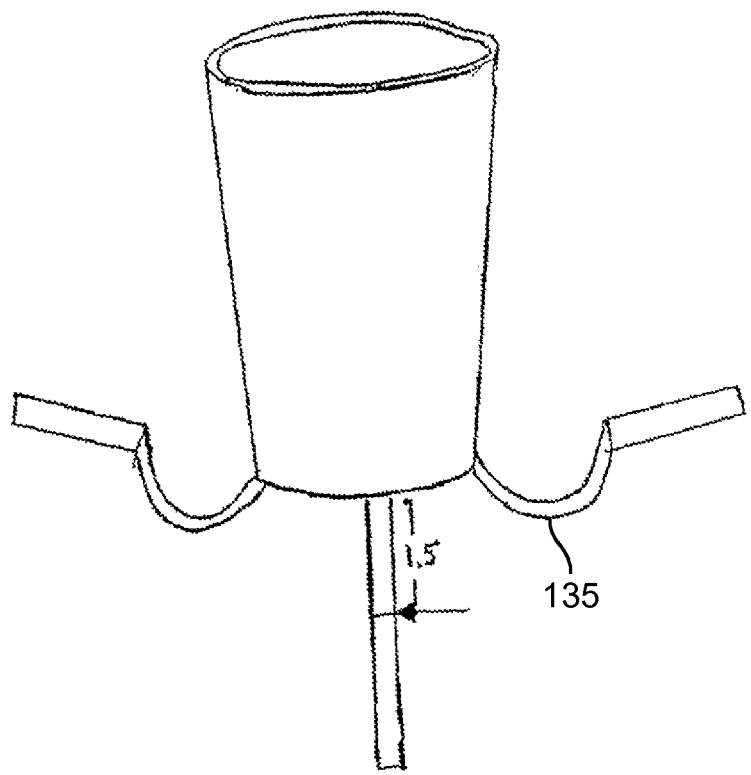
FIG. 16 is an elevational view of a four-armed tube.

FIG. 16 shows a 3-dimensional view of a multipedicle 135 tube. The inner diameter is variable as mentioned in FIG. 15.

Figure 17:
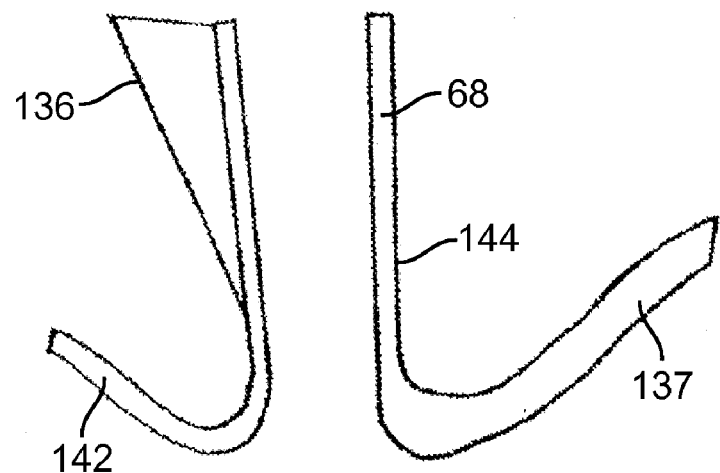
FIG. 17 is a cross-sectional view of an embodiment showing the support arms and a side element.

In another embodiment of the invention, as shown in FIG. 17, the flexible ear tube 68 is provided with a thin tab element 136 disposed preferably in a longitudinal configuration relative to an exterior surface of a stem 144 of the tube 68 to facilitate the extraction of tube 68 with an eccentric rather than linear vector. The exterior location of the element 136 is to provide a significantly preferred pulling force during the extraction of the tube 68 from an ear canal.

The tab element 136 can be of triangular shape as shown, with one of its sides fully connected to a wall segment of tube 68, or can be a simple rectangular or other shaped tab (not shown) having one of its ends or edges connected to said wall segment for pulling or extracting tube 68.

Additionally, the tube 68 has support arms 137 and 142, preferably disposed opposite to each other, the arm 137 being of a larger diameter than the diameter of the arm 142. The construction of the arm 137 is significantly sturdier, or stiffer than the construction of the arm 142.

Figure 18:
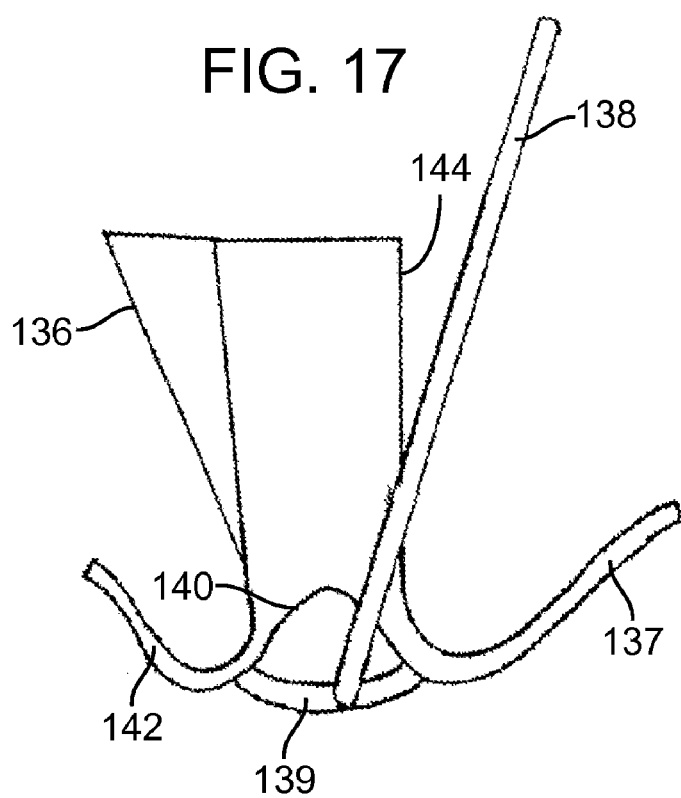
FIG. 18 is a cross-sectional view of a bridge member in another embodiment of the present invention.

In an additional embodiment of the flexible ear tube of the invention, as shown in FIG. 18, the tube is provided with a bridge element 139 attached to the two support arms 137 and 142, and enhancing their resistance to bending. Also provided is a string 138, preferably connected to an extremity of the bridge 139, and extending outwards therefrom. Preferably the string 138 is manufactured of silicone. The advantage of using the string 138 during the extraction thereof from an ear canal is the action of collapsing the bridge, thereby decreasing the inherent resistance of the bridge to be folded.

A recess 140 is provided in the material connecting the arms 137 and 142, wherein the recess 140 serves to weaken the connection between the arms sufficiently to allow for folding of the arms, thereby facilitating the extraction of the tube 68 from an ear canal.

Discussion

The tubes of the present invention differ from those of the prior art by distributing the pressure on the inner surface of the eardrum or by distancing said pressure away from the rim of the perforation. The tapered shape of the shaft resembles that in U.S. Pat. No. 4,808,171 and U.S. Pat. No. 4,775,370 but differs from them by the completely different anchoring design: while in both of the mentioned patents the anchoring area is immediately adjacent to the rim—the present invention distances the areas of contact away from the rim of the perforation.

The present invention also differs from the T tube one (U.S. Pat. No. 4,695,275) by having, in addition to the setting apart of the contact surfaces, also flat and wide contact surfaces that divides the pressure on the eardrum from its inside. That T tube has a concave contact surface that leaves a slender elongated contact line to touch the eardrum, while the present invention has a specially designed wider surface for this purpose.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A flexible ear tube for draining and ventilating the middle ear, comprising:
    a) a flexible substantially tubular stem with a lumen, said stem being sized for insertion through an incision in an eardrum; and
    b) at least two anchoring arms extending from the stem, each arm comprising a flexible member and a contact surface;
    wherein the contact surface of each arm engages a different area of the inner surface of the eardrum and is spaced apart from the stem by way of the flexible member; and
    wherein each contact surface is between 0.6 and 3 mm in width and between 1 and 7 mm in length.

2. A flexible ear tube for draining and ventilating the middle ear according to claim 1,
    wherein the ratio of the length to the width of each contact surface is between 1:6 and 1:1.

3. A flexible ear tube for draining and ventilating the middle ear according to claim 1 wherein each of said separate flexible contact surfaces has a substantially flat contact surface area of at least 1 mm$^2$.

4. A flexible ear tube for draining and ventilating the middle ear according to claim 1 wherein each of said separate flexible contact surfaces has a substantially flat contact surface area of at least 1.5 mm$^2$.

5. A flexible ear tube for draining and ventilating the middle ear according to claim 1 wherein each of said separate flexible contact surfaces has a substantially flat contact surface area of at least 2 mm$^2$.

6. A flexible ear tube for draining and ventilating the middle ear, comprising:
    a) a flexible substantially tubular stem with a lumen, said stem being sized for insertion through an incision in an eardrum; and
    b) at least two means for anchoring adapted to anchor the tube within the eardrum, each comprising a flexible member and a contact surface; wherein the anchoring means are attached at or near one of the ends of the stem; and wherein the contact surface of each anchoring means is adapted to engage a different area of the inner surface of the eardrum and is spaced apart from the stem by way of the flexible member.

7. A flexible ear tube according to claim 6 wherein said anchoring means comprise at least two spaced-apart non-linear arms extending from said stem and each provided with a contact surface at the distal end thereof.

8. A flexible ear tube according to claim 1 wherein each of said arms ascribes a substantially concave, strait arch or twisted arch.

9. A flexible ear tube according to claim 6 wherein the angle between the stem and the contact surfaces is less than 90 degrees.

10. A flexible ear tube according to claim 6 provided with a pair of opposed arched arms extending from one end of the stem.

11. A flexible ear tube according to claim 10 wherein said arms are symmetrically disposed.

12. A flexible ear tube according to claim 6 comprising at least three asymmetric arms extending from said stem.

13. A flexible ear tube according to claim 6 comprising four asymmetric arms extending from said stem, said arms including a first longer arm adapted upon insertion to be directed towards the anterior part of the tympanic cavity, a pair of relatively shorter arms adapted upon insertion to be directed superiorly and inferiorly within the tympanic cavity and a fourth relatively medium size arm adapted upon insertion to be directed towards the posterior part of the tympanic cavity.

14. A flexible ear tube according to claim 6 in combination with a flexible sleeve having a lumen sized to receive said tube comprising said stem and said anchoring means, said sleeve being provided with an open end through which said tube is insertable into a perforated eardrum.

15. A flexible ear tube according to claim 1, made of translucent material or comprising fiberoptic fibers to illuminate the inner space of the middle ear.

16. A flexible ear tube according to claim 1 that contains fiber optic filaments, through which endoscopic view of the middle ear cavity is enabled.

17. A flexible ear tube for draining and ventilating the middle ear according to claim 1, in combination with a manipulation wire extending at least 3 cm is removably attached to said tube.

18. A flexible ear tube for draining and ventilating the middle ear according to claim 17, wherein said wire has a looped form at one extremity.

19. A flexible ear tube for draining and ventilating the middle ear according to claim 17, wherein said wire holds at one extremity a guide tube, said flexible ear tube being disposed inside said guide tube.

20. A flexible ear tube for draining and ventilating the middle ear according to claim 19, wherein said guide tube is open about 100-170 degrees.

21. A flexible ear tube for draining and ventilating the middle ear according to claim 1, wherein said tubular stem is provided with a thin tab element attached to the outer portion of said stem for eccentric extraction of said flexible ear tube.

22. A flexible ear tube for draining and ventilating the middle ear according to claim 1, wherein one of said arms is of a larger diameter and is stiffer than a second opposite support arm of a second flexible contact face.

23. A flexible ear tube for draining and ventilating the middle ear according to claim 1, further provided with a bridge member attached to the two arms and a string firmly attached to said bridge member and extending outwards therefrom.

24. A flexible ear tube according to claim 6, wherein the flexible member ascribes a substantially concave, straight arch or twisted arch.

25. A flexible ear tube according to claim 6, wherein the flexible member is a folded strip.

26. A method for draining and ventilating a middle ear of a subject, the method comprising inserting a flexible ear tube according to claim 1 through an incision in the eardrum such that the contact surface of each arm engages the inner surface of the eardrum.

27. A method for draining and ventilating a middle ear of a subject, the method comprising inserting a flexible ear tube according to claim 6 through an incision in the eardrum such that the contact surface of each arm engages the inner surface of the eardrum.

28. The method of claim 27, wherein the flexible ear tube is inserted through the incision using a bent rod with a flexible sleeve having a lumen sized to receive the flexible ear tube.

29. A flexible ear tube for draining and ventilating the middle ear according to claim 1, wherein the ear tube is provided with a string configured to collapse a bridge member that bridges between the support arms during extraction of the ear tube from an ear canal.

\* \* \* \* \*